US00PP08845P

United States Patent [19]

Kriloff

[11] Patent Number: Plant 8,845

[45] Date of Patent: Jul. 26, 1994

[54] HYBRID TEA ROSE PLANT NAMED 'KRIMONY'

[75] Inventor: Michel Kriloff, Antibes, France

[73] Assignee: The Conard-Pyle Company, West Grove, Pa.

[21] Appl. No.: 74,760

[22] Filed: Jun. 10, 1993

[51] Int. Cl.[5] ..... A01H 5/00
[52] U.S. Cl. ..... Plt./11
[58] Field of Search ..... Plt. 11, 12, 22

*Primary Examiner*—Howard J. Locker
*Attorney, Agent, or Firm*—Burns, Doane, Swecker & Mathis

[57] ABSTRACT

A new and distinct variety of Hybrid Tea rose plant is provided which abundantly forms attractive very double long-lasting bicolor blossoms which are Scarlet Pink suffused with Primrose Yellow on the upper side, and Primrose Yellow slightly edged and suffused with Carmine Rose on the under side. The blooms exhibit a very elegant configuration and are borne on very long straight stems. The plant exhibits an upright growth habit, forms vigorous vegetation, and is particularly well suited for cut flower production since it exhibits an excellent ability to be forced under greenhouse growing conditions. Additionally, the plant exhibits very good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Krilami variety (non-patented in the United States). The male parent (i.e., the pollen parent) was the product of the pollination of an unnamed seedling by the Kricarlo variety (U.S. Plant Pat. No. 5,165). The parentage of the new variety can be summarized as follows:

Krilami × (Unnamed Seedling × Kricarlo).

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long-lasting very double blossoms which are Scarlet Pink suffused with Primrose Yellow on the upper side and Primrose Yellow slightly edged and suffused with Carmine Rose on the under side,
(b) forms blooms that exhibit a very elegant configuration,
(c) forms dark green adult wood,
(d) exhibits vigorous vegetation,
(e) exhibits an upright growth habit,
(f) exhibits an excellent capacity to be forced under greenhouse conditions and is particularly well suited for cut flower production, and
(g) is not particularly affected by cryptogamic diseases.

The new variety has been found to undergo asexual propagation by a number of routes, including budding, grafting, cuttage, etc. The characteristics of the new variety have been found to be strictly transmissible by such asexual propagation from one generation to another in France and in the United States.

The new variety has been named the Krimony variety.

BRIEF DESCRIPTION OF THE PHOTOGRAPH

The accompanying photograph shows as nearly true as it is reasonably possible to make the same, in a color illustration of this character, typcial specimens of the plant parts of the new variety. The rose plants of the new variety were one year of age and were observed during April while budded on *Rosa indica* understock and growing in greenhouses at Cap d' Antibes, France.

DETAILED DESCRIPTION

Figures 1, 2, 3, 4, 5, 6, 7, 8, 9, 10, 11, 12, 13, 14, 15:
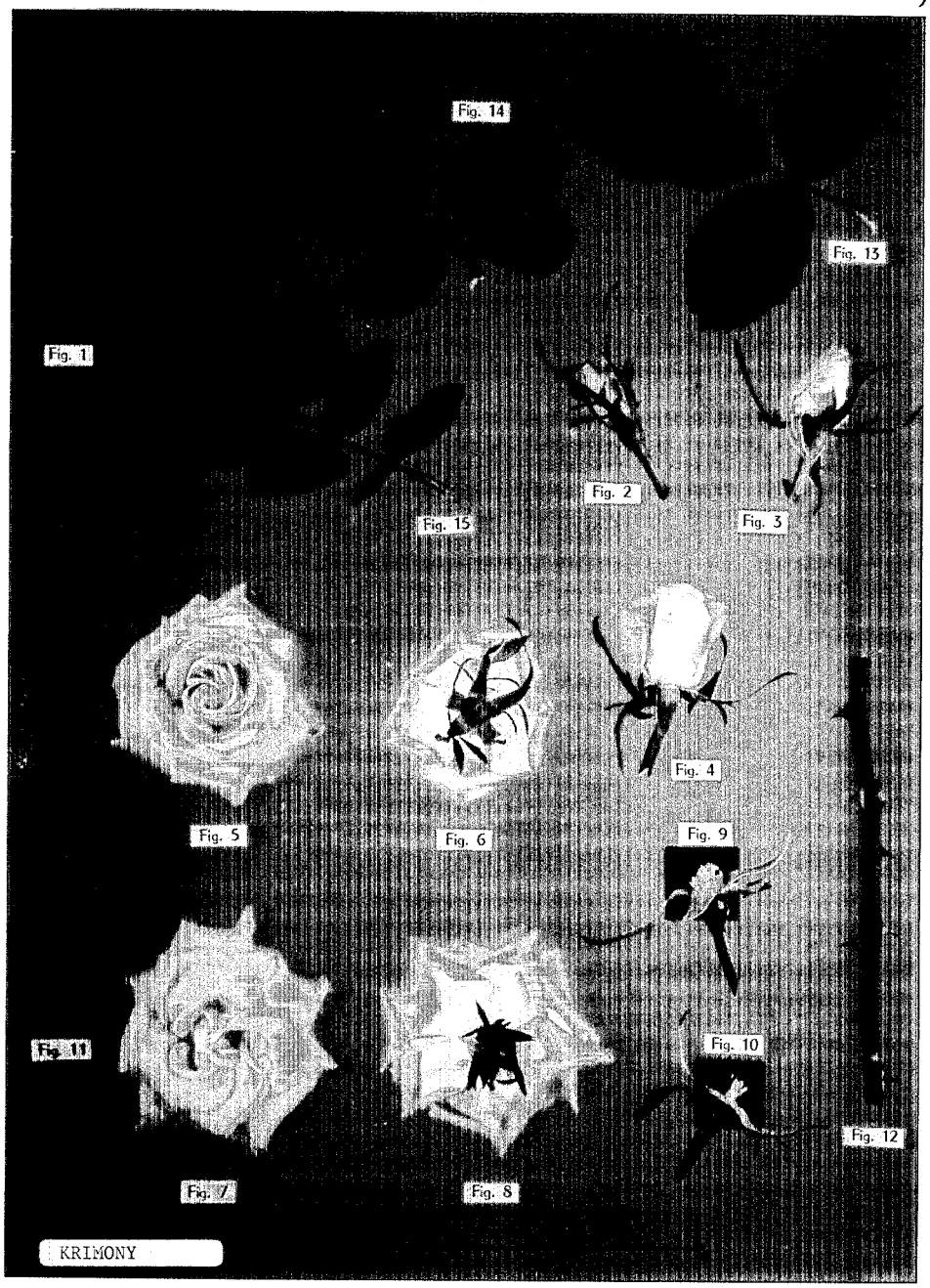
FIG. 1 illustrates a specimen of a young shoot.
FIG. 2 illustrates a specimen of a floral bud at the opening of the sepals.
FIG. 3 illustrates a specimen of a floral bud at the opening of the petals.
FIG. 4 illustrates a specimen of a flower in the course of opening.
FIG. 5 illustrates a specimen of an open flower — plan view — obverse.
FIG. 6 illustrates a specimen of an open flower — plan view — reverse.
FIG. 7 illustrates a specimen of a fully open flower — plan view — obverse.
FIG. 8 illustrates a specimen of a fully open flower — plan view — reverse.
FIG. 9 illustrates a specimen of a floral receptacle showing the arrangement of the stamens and pistils.
FIG. 10 illustrates a specimen of a floral receptacle showing the arrangement of the pistils (stamens removed)
FIG. 11 illustrates a specimen of a flowering stem.
FIG. 12 illustrates a specimen of a main branch.
FIG. 13 illustrates a specimen of a leaf with three leaflets — plan view — upper surface.
FIG. 14 illustrates a specimen of a leaf with five leaflets — plan view — under surface.
FIG. 15 illustrates a specimen of a leaf with seven leaflets — plan view — upper surface.

The chart used in the identification of the colors is that of The Royal Horticultural Society (R.H.S. Colour Chart). The description is based on the observation of one year old plants made during April while budded on *Rosa indica* understock and growing in greenhouses at Cap d' Antibes, France. The coloration in common terms precedes reference to the chart.

Class: Hybrid Tea.

Plant:

*Height.*—When plants are cut to a height of 85 cm., flowering stems having lengths of approximately 50 to 80 cm. commonly are formed. When grown outdoors in fields at Wasco, Calif., at the end of one growing season, the plants commonly have a height of approximately 120 to 130 cm.

*Habit.*—Upright.

Branches:

*Color.*—Young Stems: bronze green, Yellow-Green Group 146A. Adult wood: dark green, Green Group 137A.

*Thorns.*—Size: large. Quantity: numerous. Color: greenish-pink on young stems and greenish changing to tan on mature wood.

Leaves:

*Stipules.*—Adnate, pectinate, wide and linear.

*Petioles.*—Upper surface: striped reddish brown on young foliage and medium green on mature foliage with more or less glandular edges. Under surface: light green, and bears a few prickles.

*Leaflets.*—Number: 3, 5 (most often), and 7. Shape: elliptic. Serration: single and regular. Texture: leathery. General appearance: bright and fairly dense foliage. Color (young foliage): Upper surface: medium green, Yellow-Green Group 146B, and widely suffused with reddish coloration. Under surface: light reddish-brown in coloration. Color (adult foliage): Upper surface: dark green, Green Group 137A. Under surface: light green, Green Group 137C.

Inflorescence:

*Number of flowers.*—Usually one single bloom per stem.

*Peduncle.*—Medium green and very long. The length is approximately 12 to 16 cm. on average.

*Sepals.*—Upper surface: tomentose, greenish in coloration. Under surface: medium green, the outer sepals are more or less glandular and often end in a well developed leaf-like appendix.

*Buds.*—Shape: conical. Length: approximately 3 cm. on average. Size: medium. Color upon opening: Upper surface: Mandarin Red, Red Group 40B, edged with Dutch Vermilion, Red Group 40A, and suffused with Canary Yellow, Yellow Group 9B. Under surface: light yellow, Yellow Group 3C, and widely suffused with cherry red, Red Group 45C.

*Flower.*—Shape: cup-like and very double. Diameter: approximately 11 to 12 cm. on average when fully open. Color (when opening begins): Upper surface: Scarlet Pink, Red Group 43C on the edges turning to light Scarlet Pink, Red Group 43D towards the center and suffused with Primrose Yellow, Yellow Group 4D. Under surface: Primrose Yellow, Yellow Group 4D edged with deep Carmine Pink, Red Group 52A, and suffused with light Carmine Rose, Red Group 52D. Color (when blooming): Upper surface: Scarlet Pink, Red Group 43C towards the center of the petals and suffused with Primrose Yellow, Yellow Group 4D. Under surface: Primrose Yellow, Yellow Group 4D edged with deep Carmine Pink, Red Group 52A, and suffused with light Carmine Rose, Red Group 52D. Color (at end of opening): Upper surface: Scarlet Pink, Red Group 43C on the edges turning to light Scarlet Pink, Red Group 43D towards the center and suffused with Primrose Yellow, Yellow Group 4D, with the general aspect being lighter than at the earlier stages. Under surface: Primrose Yellow, Yellow Group 4D, edged with Carmine Pink, Red Group 52A, and suffused with light Carmine Rose, Red Group 52D, with the general aspect being lighter than at the earlier stages. Fragrance: none. Lasting quality: very long when cut and placed in a vase. Petal number: approximately 38 to 42 on average. Petal shape: oval, narrower toward the center of the bloom, with reflective lateral sides. Texture: consistent. Petal drop: good. Stamen number: approximately 55 to 62 on average. Anthers: normal, ochre in coloration, and commonly located below the pistils. Filaments: yellowish in coloration, more or less tinted with pinkish coloration, and relatively short in height. Pistils: approximately 60 to 64 on average. Stigmas: normal and yellowish in coloration. Styles: tomentose near the base, and of light fuchsia coloration. Receptacle: light green in coloration, smooth, and in longitudinal section it is in the shape of a funnel at the dehiscence of the anthers.

Development:

*Vegetation.*—Vigorous.

*Blooming.*—Abundant.

*Resistance to diseases.*-Very good.

*Aptitude to be forced.*—Excellent.

I claim:

1. A new and distinct variety of Hybrid Tea rose plant characterized by the following combination of characteristics:

(a) forms in abundance attractive long-lasting very double blossoms which are Scarlet Pink suffused with Primrose Yellow on the upper side and Primrose Yellow slightly edged and suffused with Carmine Rose on the under side, (b) forms blooms that exhibit a very elegant configuration, (c) forms dark green adult wood, (d) exhibits vigorous vegetation, (e) exhibits an upright growth habit, (f) exhibits an excellent capacity to be forced under greenhouse conditions and is particularly well suited for cut flower production, and (g) is not particularly affected by cryptogamic diseases;

substantially as herein shown and described.

* * * * *

KRIMONY